United States Patent [19]

Munoz

[11] Patent Number: 5,762,811
[45] Date of Patent: Jun. 9, 1998

[54] ONE-SIDED PHOTOETCHING PROCESS FOR NEEDLE FABRICATION

[75] Inventor: Marcelino P. Munoz, Waterbury, Conn.

[73] Assignee: United States Surgical Corporation, Norwalk, Conn.

[21] Appl. No.: 590,715

[22] Filed: Jan. 24, 1996

[51] Int. Cl.$^6$ .................................. B21G 3/18; B44C 1/22
[52] U.S. Cl. ........................... 216/11; 216/100; 430/320; 430/323; 606/223
[58] Field of Search ........................................ 216/11, 100

[56] References Cited

U.S. PATENT DOCUMENTS

| | | | |
|---|---|---|---|
| 2,242,967 | 5/1941 | Carlile | 85/49 |
| 2,326,022 | 8/1943 | Everett | 113/112 |
| 2,469,689 | 5/1949 | Gresham | 204/24 |
| 2,479,464 | 8/1949 | Bliss | 128/339 |
| 2,735,763 | 2/1956 | Heath | 95/5.7 |
| 3,038,475 | 6/1962 | Orcutt | 128/339 |
| 3,054,172 | 9/1962 | Turney, Jr. | 29/413 |
| 3,162,871 | 12/1964 | Powers | 10/54 |
| 3,348,669 | 10/1967 | Powers | 206/56 |
| 3,358,363 | 12/1967 | Jacks et al. | 29/623 |
| 3,551,227 | 12/1970 | Burgess | 156/13 |
| 3,808,001 | 4/1974 | Konstantouros et al. | 96/36 |
| 3,816,273 | 6/1974 | Snyder | 204/129.9 |
| 3,822,461 | 7/1974 | Malmstrom | 29/415 |
| 3,942,981 | 3/1976 | Sato | 96/36 |
| 4,080,709 | 3/1978 | Poler | 29/412 |
| 4,215,194 | 7/1980 | Shepherd | 430/323 |
| 4,282,311 | 8/1981 | Dinardo, Jr. | 430/318 |
| 4,587,202 | 5/1986 | Borysko | 430/320 |
| 4,672,734 | 6/1987 | Kawada et al. | 29/517 |
| 4,711,800 | 12/1987 | DiVincenzo | 428/131 |
| 4,777,096 | 10/1988 | Borysko | 428/571 |
| 4,785,868 | 11/1988 | Koenig, Jr. | 163/5 |
| 4,793,218 | 12/1988 | Jordan et al. | 76/101 R |
| 4,842,969 | 6/1989 | Kawatsuki et al. | 430/5 |
| 4,890,614 | 1/1990 | Kawada et al. | 600/339 |
| 5,001,323 | 3/1991 | Matsutani et al. | 219/121.63 |
| 5,057,401 | 10/1991 | Borysko et al. | 430/320 |
| 5,178,628 | 1/1993 | Otsuka et al. | 606/223 |
| 5,330,441 | 7/1994 | Prasad et al. | 606/222 |
| 5,403,344 | 4/1995 | Allen | 606/223 |
| 5,411,613 | 5/1995 | Rizk et al. | 148/606 |
| 5,478,344 | 12/1995 | Stone et al. | 606/144 |

FOREIGN PATENT DOCUMENTS

| | | |
|---|---|---|
| 24 05 998 A1 | 2/1974 | Germany. |
| 27 37 648 A1 | 8/1977 | Germany. |
| 34 14 262 A1 | 4/1984 | Germany. |

OTHER PUBLICATIONS

Yashiro et al., "A Method of Specimen Preparation for FIM and FEM," Surface Science, vol. 67, pp. 607–610, 1977.
Y. Yashiro et al., "A Method of Specimen Preparation For FIM and FEM", Surface Science 67 (1977) 606–610 Steel, Photoetching Forms Thin Parts. vol. 141, No 21 (Nov. 1957) 153–156.

*Primary Examiner*—R. Bruce Breneman
*Assistant Examiner*—Michael E. Adjodha

[57] ABSTRACT

Surgical needles are fabricated by masking and etching a plurality of the needle blanks from one side of a base material, such as a metal sheet, after applying an etchant resistant adhesive backing to the other side and then etching the one side of the sheet as a chemical milling process. The resultant needles are unattached to each other or to the sheet and individually removable from the backing. This increases the speed of manufacturing while maintaining the ease of use.

22 Claims, 7 Drawing Sheets

ONE-SIDED PHOTOETCHING PROCESS FOR NEEDLE FABRICATION

BACKGROUND

1. Technical Field

This disclosure relates to surgical needles, and more particularly, to a method for photoetching multiple needles simultaneously.

2. Background of Related Art

Processes for preparing quality needles from raw stock typically include the steps of straightening spooled wire stock, cutting needle blanks from raw stock, tapering or grinding points on one end of the blank, providing a bore for receiving suture thread at the other end of the blank, flat pressing a portion of the needle barrel to facilitate easier grasping by surgical instrumentation, and curving the needle blank.

Most surgical needle blanks are typically made one at a time. However, it is increasingly difficult to maintain the precision quality of very small needles, e.g. needles used in microscopic surgery, such as ophthmic needles. Each needle must be cut, formed and sharpened, in order to yield uniform surgical needles.

An alternative to individually fabricating surgical needles is to simultaneously form a plurality of needles from a metal base plate using a photoetching technique.

The basics of this technique are well known in the art. The first step is to coat a thin metal sheet with a light sensitive, photoresist material. This can be done by conventional methods such as dipping or spraying the metal with any commercially available photoresist. Alternatively, a dry photoresist attached to a film may be applied to the metal sheet. The metal is typically repeatedly cleaned, rinsed and briefly immersed in a diluted aqueous acid, such as 10% HCl before being coated. The coating itself should be done under safe light conditions, e.g. yellow or orange light, to prevent exposing the entire sheet. The coated sheet is lightly baked for a few minutes at about 80° C. in order to speed up and ensure the drying of the coat. A negative image of the product to be fabricated is placed over the coated metal and then exposed to light. A light rich in ultraviolet radiation, such as carbon-arc or mercury vapor lamps are preferred, but any ultraviolet rich fluorescent light may be used. This typically hardens the photo resist while removing the non-exposed areas of the coating. The negative image is removed and the metal sheet is subsequently placed in an etchant solution, such as an aqueous solution of ferric chloride and HCl, where the unwanted, uncoated metal is etched away. The desired product, such as the plurality of needles are left.

As a final step, these are washed, dried, and stripped of any remaining photoresist.

This technique generates a plurality of surgical needle blanks attached at their respective suture attachment ends to a supporting base strip. See, e.g. U.S. Pat. Nos. 4,587,202 and 4,777,096, both to Borysko.

A second technique entails photoetching both sides of a metal sheet to form the needle blanks with an attached carrier strip. An adhesive backing is then applied to one side of the blank and the blank is then etched a second time. This eliminates the carrier strip as well as the need to further polish the needles. Accordingly, a need exists for a photoetching process that results in a predetermined needle cross section without a separate pressing step while also permitting collective needle manufacturing and finishing.

SUMMARY

A photoetching process for fabricating surgical needles is disclosed in which a top side of a base material is coated with a light sensitive photoresist material and a layer of material with an adhesive backing is attached to the bottom side. A mask in the negative image of the needle blanks to be fabricated is placed over the photoresist and then exposed to light. The unexposed areas are then etched away through the material, completely etching away those areas. The negative image is such that the needle blanks do not remain attached to each other by any type of carrier strip. The negative image is removed and the etching process is repeated on the top side as a chemically milling step, leaving individual finished needles attached to the adhesive backing without any carrier strip. This process allows for the generation of predetermined needle cross-sections without pressing and permits subsequent collective electropolishing of all the needle blanks simultaneously.

BRIEF DESCRIPTION OF THE DRAWING

Various embodiments are described herein with reference to the drawings wherein.

DETAILED DESCRIPTION OF PREFERRED EMBODIMENTS

In the drawings and in the description which follows, the term "proximal", as is traditional, will refer to the end of the structure which is closest to the user, i.e., the suture end of the needle, while the term "distal" will refer to the end of the structure which is furthest from the user, i.e. the point. As used herein, the term "surgical needle blank" refers to a piece of needle stock material at various stages of completion but not fully formed into a surgical grade needle suitable for use during surgical procedures. Needles suitable for such procedures will be referred to as "surgical needles".

Figure 1:
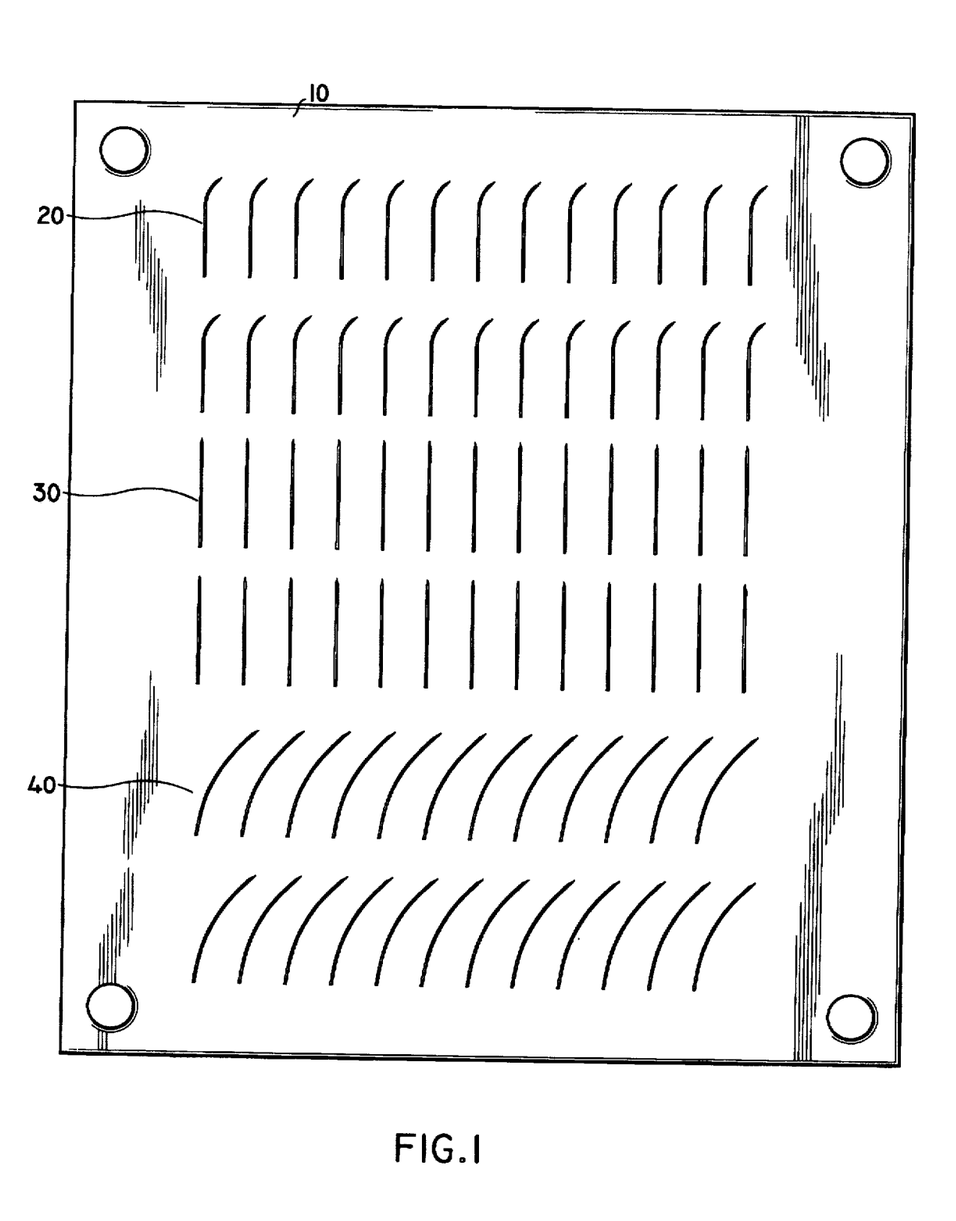
FIG. 1 is a top view of a series of surgical needle blanks on an adhesive backing in accordance with the present disclosure.

Referring now to the drawings wherein like reference numerals identify similar structural or procedural elements, there is illustrated in FIG. 1 a sheet 10 of surgical needle blanks fabricated in accordance with a preferred embodiment. As will become readily apparent to those having ordinary skill in the art, surgical needle blanks are fabricated in such a manner so as to reduce the costs associated with this fabrication as compared to prior art surgical needle blanks. It will also become readily apparent that the surgical needle blanks do not require a tree or carrier strip connecting the needle blanks.

The needle blanks are fabricated by chemically etching away unwanted material from the top side of the sheet, while attaching an etch-resistant adhesive backing to the bottom side. A second etching is then performed to remove any remaining unwanted material as a chemical milling step.

Because of their symmetry, needle blanks of similar types are fabricated next to each other in order to maximize the number of needle blanks fabricated on any one sheet.

Therefore, as shown in FIG. 1, slightly curved needle blanks 20 can be fabricated on the same sheet as highly curved needle blanks 40 and straight needle blanks 30. These needle blanks may vary in size, as well as in shape.

Figure 2:
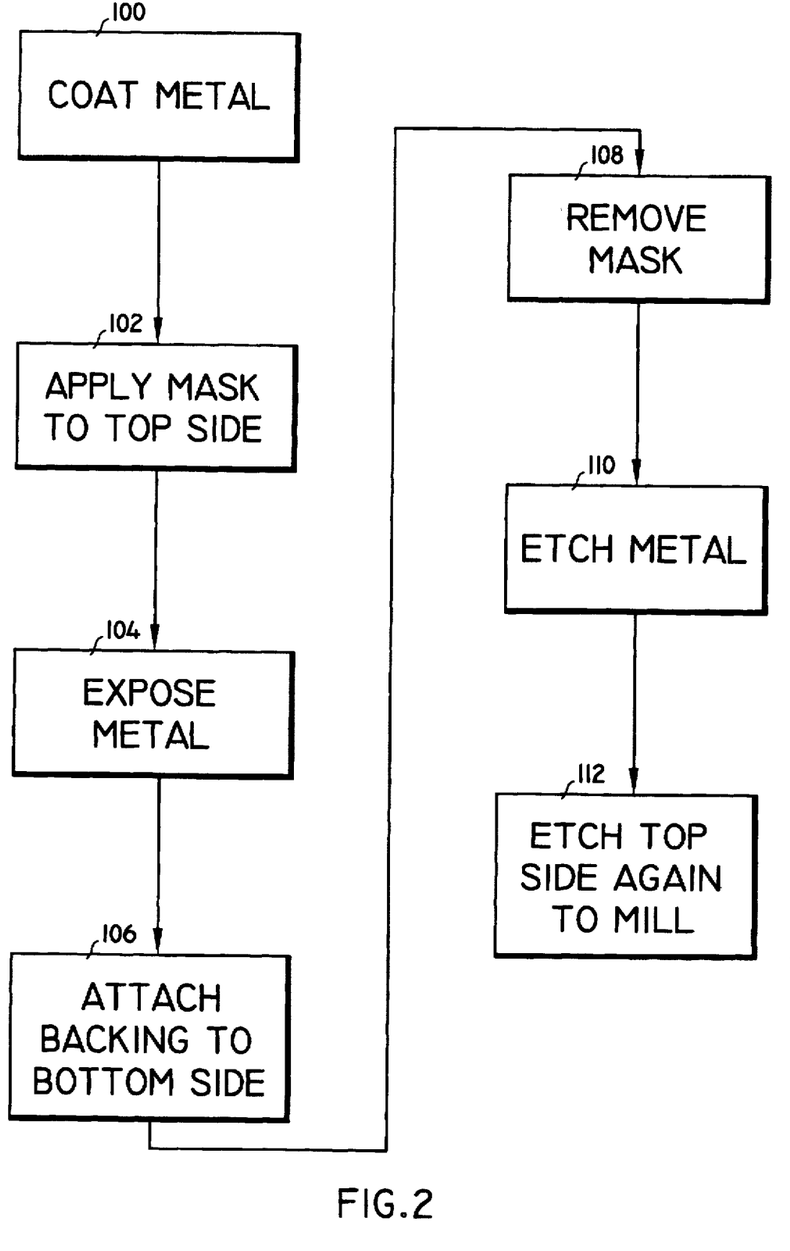
FIG. 2 is a flow diagram showing the steps of a needle fabricating method in accordance with the present disclosure.

FIG. 2 shows the overall flow of the various steps making up a preferred embodiment of the present disclosure. Each step is shown in parentheses in the following example and further shown in each of the subsequent figures.

Initially, a metal sheet, preferably Sandvik 1RK91 or Carpenter 455 stainless steel, as disclosed in U.S. Pat. No. 5,411,613, is coated with a photoresist material (100), such as "KMER" or "RISTON", available from DuPont. The photoresist material is of a type which, when exposed to light and subsequently developed, becomes hard and resistant to an etching solution, but unless exposed to light, can be readily removed by washing. This coating step is done either in darkness, or in a safe-light condition, e.g. yellow or orange light, typically by dipping the metal sheet into the photoresist, but can also be sprayed or brushed on. This safe-light condition prevents the entire surface from being exposed and acted upon before it has been completely prepared. A mask having a negative image of the series of needle blanks to be fabricated is positioned over the coated top surface of the material (102). The negative image used for the photoresist process can be made on, for example, a glass plate, increasing the amount of times it can be reused.

The surface of the metal sheet is then exposed to preferably an ultraviolet rich light through the negatives so that the light only acts on those areas aligned with the reproduction of the needle blanks (104).

The exposed sheet is then developed in any one of several commercially available developers, and washed to remove the light-sensitive material not acted on by the light. The sheet thus has imposed on it a positive image of the shape of the desired needles. The plate with the negative image of the needle blanks is now removed.

The entire bottom surface is then coated with an etchant resistant material such as solutions from the vinyl copolymer group (106). This coating can be brushed or sprayed on so that it can readily be removed by, for example, immersing the sheet in a suitable dissolving solvent as described above. As an alternative, the coating can be applied as a thin layer having an adhesive backing.

Figure 4:
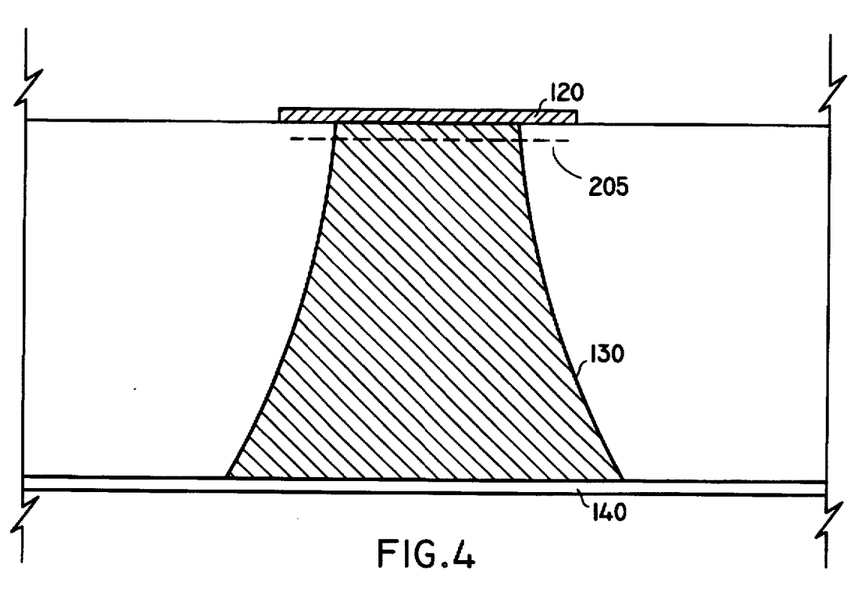
FIG. 4 is a cross-sectional view of a single needle blank after etching in accordance with the method of the present disclosure.

As shown via a cross-sectional view of an individual needle blank in FIG. 4, the sheet 10 is then immersed in an etchant solution (108), such as 36 to 42 degrees Celsius Baumé aqueous ferric chloride, or an aqueous solution of hydrochloric acid and either ferric chloride or nitric acid, where the metal is dissolved from the areas not covered by the etchant-resistant, photo-sensitive material 120. The sheet is immersed just long enough so that approximately 50% of the thickness of the uncovered metal 130 is etched away.

This will form an almost squared off shape. The additional bottom edges will improve the ease of penetration into the tissue and the like.

Figure 5A:
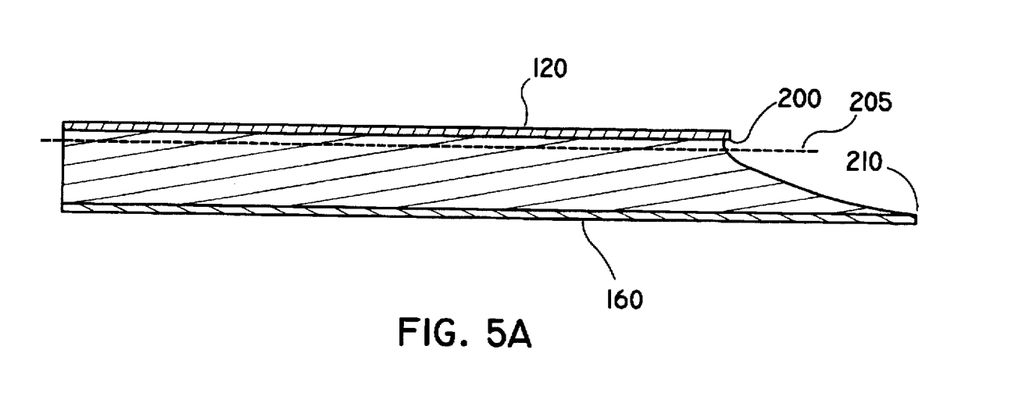
FIG. 5A is a side view of a surgical needle blank fabricated in accordance with the present disclosure prior to milling.

The metal sheet is washed, dried and stripped of any remaining photoresist by any suitable commercial stripper (110). The metal sheet with the resistant backing is now immersed in a weakened form of the etching solution for a short period of time. This will chemically mill the metal (112) to remove a top layer of the material designated by the dotted line 205 in FIG. 5A. This milling removing any burrs and sharpening the sides and edges of the needle blank. The further step of individually grinding and polishing the needles is thus eliminated. The second etching process cleanly sharpens the sides and tip of the needle blanks as well as removes any rough edges, flairs or burrs left from the initial etching due to the masking process as depicted in FIG. 5A. This chemical milling process leaves the sides much smoother and straighter than the typical electropolishing bath of, for example, an aqueous sulfuric, phosphoric and glycolic acid bath.

After the final etching, the metal sheet is again washed and dried to remove any remaining etching solution. A finished set of sharpened needles on the backing is ready for use. The needles may either be removed individually from the adhesive backing or washed in a stripper as a dissolving solvent commercially available and formulated for the particular coating used.

Figure 5B:
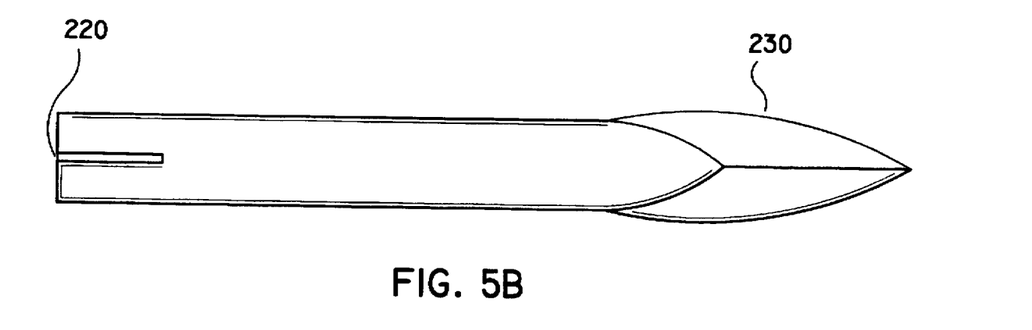
FIG. 5B is a top view of the surgical needle blank of FIG. 5A.
Figure 5C:
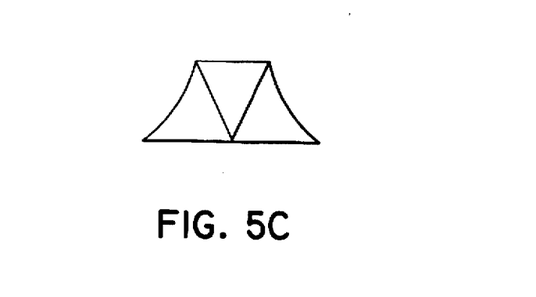
FIG. 5C is a front view of the surgical needle blank of FIG. 5A.

As a further embodiment to the present disclosure, a channel or grove 220 may be etched directly into the proximal end of the needle blank to simplify attaching a suture by clamping or crimping means as shown in FIG. 5B. This eliminates the need to drill a hole or channel after the needle is formed.

In an alternate embodiment, the sides of the distal, sharpened end of the needle may be bowed out in a spatula design 230. This is in order to further ease penetration into the tissue.

Figure 6A:
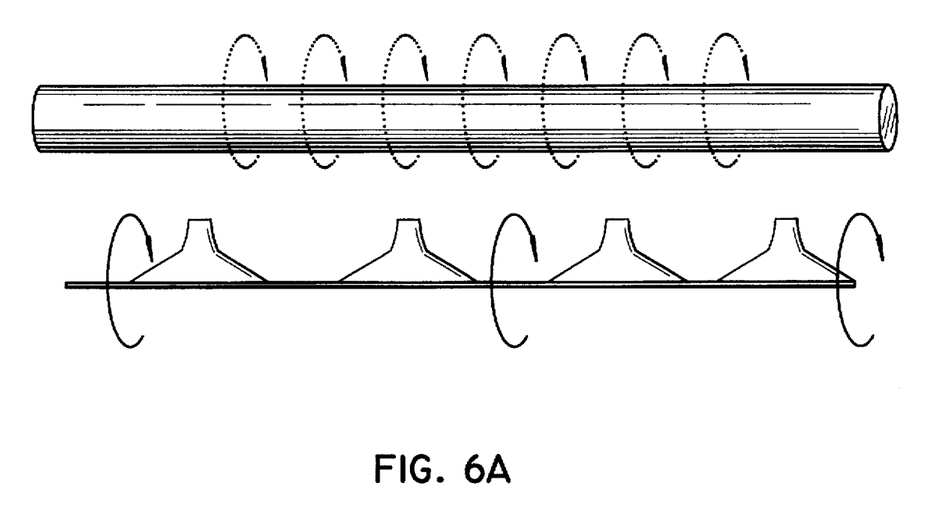
FIG. 6A is a side view of an illustration of electromagnetic curving of the surgical needle blanks in accordance with the present disclosure.
Figure 6B:
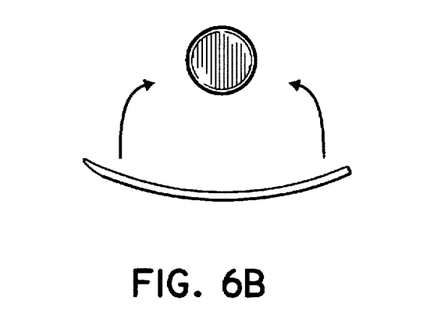
FIG. 6B is an end view of an illustration of electromagnetic curving of the surgical needle blanks in accordance with the present disclosure.

In another embodiment, all the needles on the sheet are etched as straight needles. These are then placed under a mandrel as illustrated in FIGS. 6A and 6B, perpendicular to the mandrel's rolling surface. Typically, the needles are rolled and pressed around the mandrel using typically a series of belts. In this embodiment, both the needle containing sheet and the mandrel are electromagnetically charged with opposite charges. Typically, this will be in the order of 3K–4K Gauss. The electromagnetic attraction between the needle containing sheet and mandrel will bend the needle around the mandrel without the need for direct contact. It is also contemplated that a backing sheet may be associated with the needle-containing sheet to capture and control bending of the needles. Preferably, the backing sheet is a flexible metal sheet electro-magnetically charged with the same charge as the needle-containing sheet.

FIGS. 3A through FIG. 3D depicts the following example as it illustrates the advantages achieved by the present method. A metal sheet of Sandvik 1RK91 is cut to a specified size and thickness, and is then cleaned with a diluted solution of 10% HCL (step 200, 300). This removes any debris left from the cutting and handling of the sheet. A thin layer of a commercial photoresist is brushed onto both sides of the metal sheet (step 202, 302). The sheet is then mildly heated for a few minutes to ensure that the photoresist is dried onto the entire sheet (step 204, 304). A negative image of the top of a series of needles is placed on the top side of the sheet (steps 206, 306). The image is slightly larger than the final configuration of the desired needles in order to compensate for any subsequent loss due to the etching and milling processes and is used as a mask for areas not to be hardened by the photoresist.

Figure 3A:
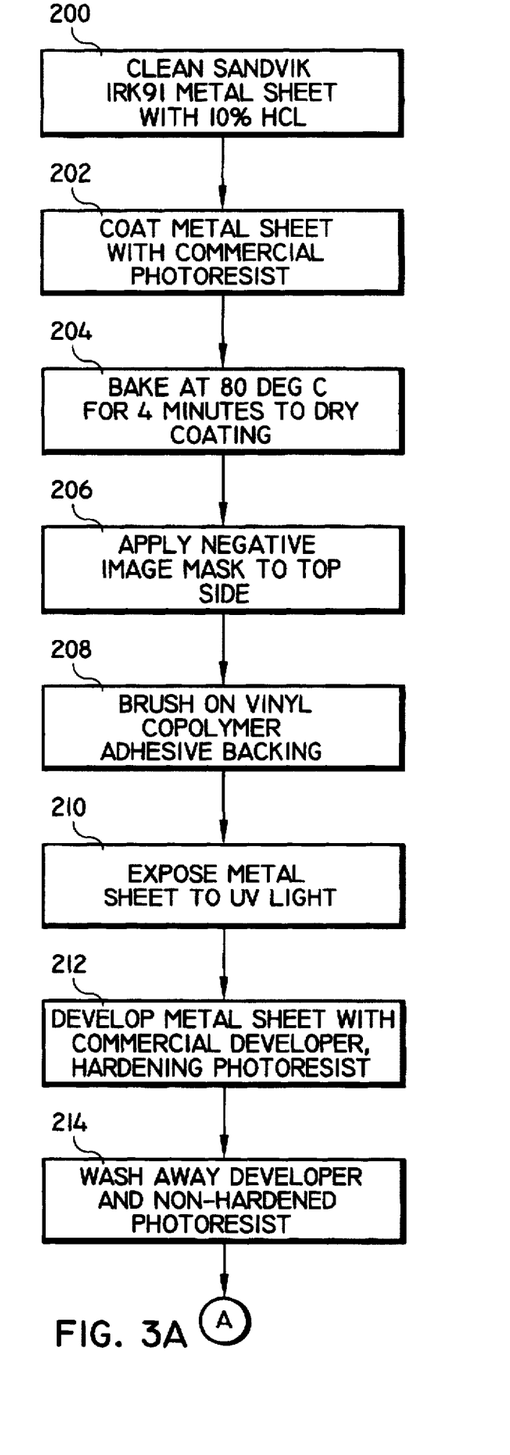
FIGS. 3A and 3B are flow diagrams showing an illustrative example of a needle fabricating method in accordance with the present disclosure.
Figure 3B:
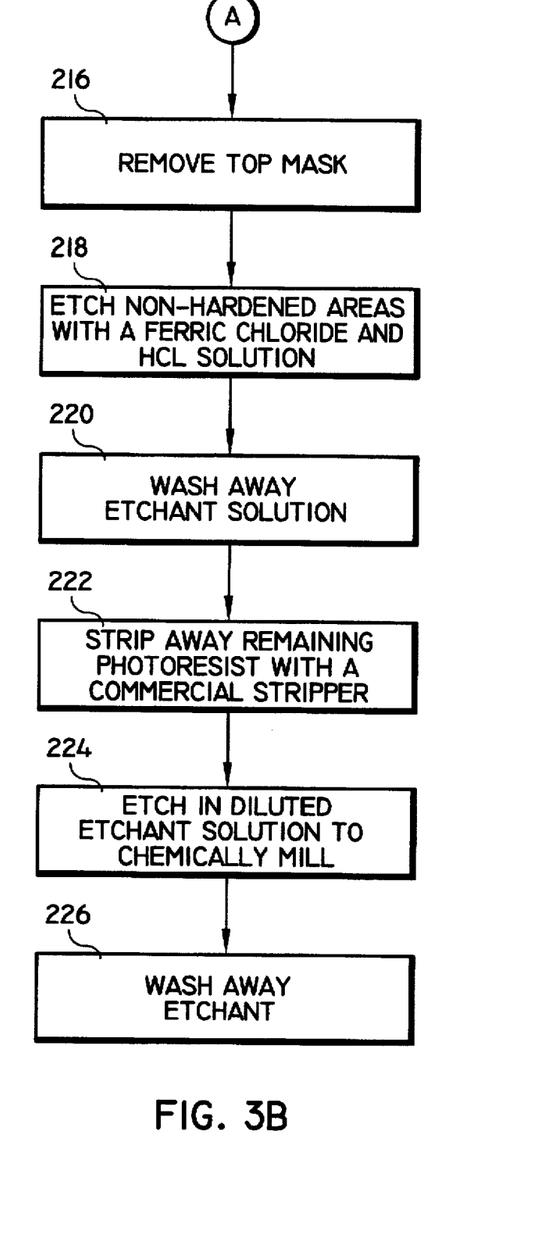
Figure 3C:
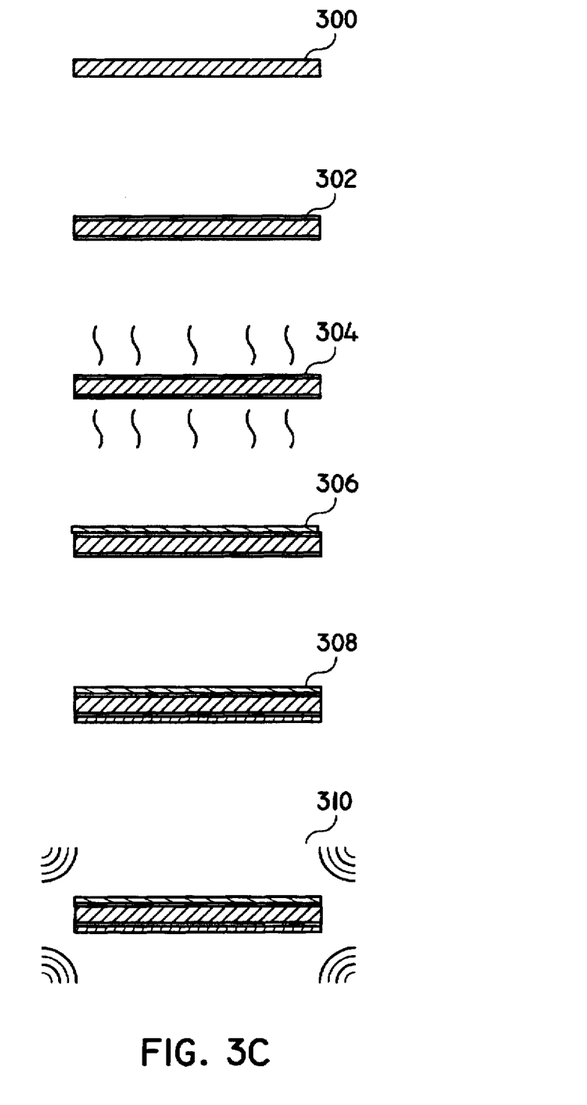
FIGS. 3C and 3D are a series of sectional views corresponding to the steps of FIGS. 3A and 3B respectively.

A thin layer of a vinyl copolymer is brushed on the bottom side of the metal sheet (step 208, 308). This coating forms an adhesive backing, further securing the needles to each other.

The encased metal sheet is subjected to a mercury vapor lamp that is high is ultraviolet light (step 210, 310). After being exposed to the ultraviolet light, the sheet is immersed in a commercial developer, hardening those areas that were exposed to the light (step 212). Once the exposed areas have hardened, the metal sheet is washed (step 214) to remove the developer and any non-hardened photoresist. The negative image mask is removed (step 216, 312) from the surface of the metal sheet.

Figure 3D:
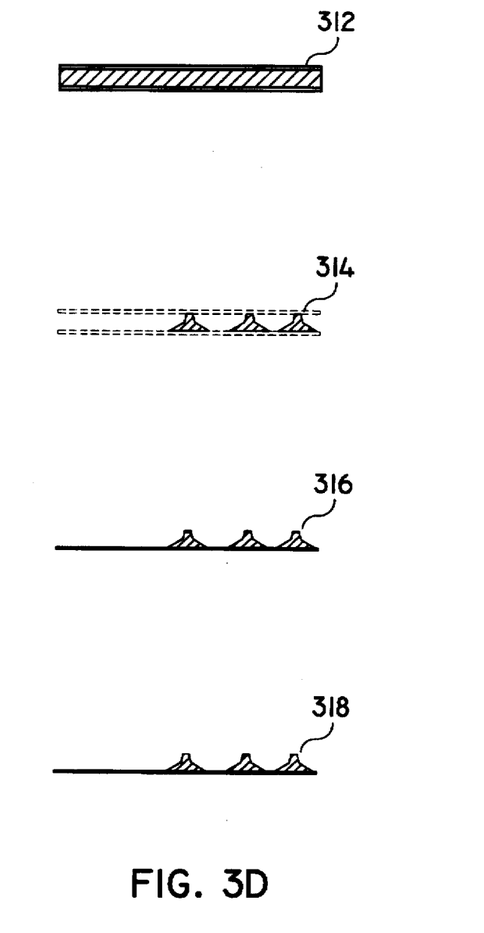

The metal sheet is then immersed in an aqueous solution of ferric chloride and HCL (step 218, 314) until approximately 65% of the uncoated, unprotected metal has been etched away from each side. At that point in time, the sheet is removed from the etchant solution and the solution is washed away (step 220). The needles are captured on the adhesive backing. The photoresist on the non-etched areas is stripped away (step 222, 316) by a commercial stripper appropriate for the particular photoresist used.

The secured needle blanks are immersed in a diluted version of the etchant solution (step 224). This will have the effect of chemically milling the top side of the needle blanks and sharpening the edges of the needle blanks. The etchant solution is washed away (step 226, 318) stopping the etching process and leaving finished needles on the adhesive backing.

Table II shows average bend movement for commercial square bodied curved needles and square bodied curved needles photoetched in accordance with the disclosure from the preferred Sandvik 1RK91 material, with and without heat treatment. Bend movement tests were conducted in accordance with U.S. Pat. Nos. 5,022,273 and 5,297,440.

TABLE II

| | MATERIAL | NO. OF SAMPLES | AVERAGE BEND MOVEMENT (gmXcm) |
|---|---|---|---|
| Comparative Example 1 | Sandvik 1RK91 (.006 inch diameter) wire mechanically formed into square body curved needle, heat treated (USSC code mv-135-5) | 13 | 10.56 |
| Comparative Example 2 | Ethicon TG 160-6 .006 inch diameter wire square bodied curved needle | 6 | 6.07 |
| Example 1 | Sandvik 1RK91 sheet (.006 inch thickness) photoetched square bodied curved needle | 10 | 10.09 |
| Example 2 | Sandvik 1RK91 sheet (.006 inch thickness) photoetched square bodied curved needle, heat treated (475° C. for 4 hours) | 10 | 19.06 |

It will be understood that various modifications may be made to the embodiments disclosed herein. For example, a sheet of nylon or polyamide film can be used in the etched-metal technique described above. In this case, the photoresist coating is, for example, by a deposition of chromium on the plastic. The etchant solution would be a solution of hydrazine hydride. Therefore, the above description should not be construed as limiting, but merely as exemplifications of preferred embodiments. Those skilled in the art will envision other modifications to the disclosure within the scope and spirit of the claims appended hereto.

What is claimed is:

1. A method for fabricating surgical needle blanks comprising the steps of:
   selectively masking a first side of an unmasked sheet of base material into chemically resistant patterns corresponding to a plurality of individual surgical needles;
   exposing unmasked areas of said masked base material to light to form an etchant resistant coating thereon;
   applying an etchant resistant backing to a second side of said base material;
   etching away from said base material those areas which do not have said etchant resistant coating to form a sheet with a plurality of individual surgical needle blanks attached to said etchant resistant backing; and
   removing said etchant resistant coating from said plurality of individual surgical needles.

2. The method of claim 1, wherein the step of masking includes masking said first side of said base material into patterns corresponding to a plurality of individual surgical needles of various shapes.

3. The method of claim 1, wherein said masking comprises the steps of:
   coating only said first side of said base material with a photo-resistant material; and
   covering said first side of said coated base material with a negative image of a first side of said plurality of individual surgical needles.

4. The method of claim 3, wherein said negative image is on a glass plate.

5. The method of claim 3, wherein the step of masking further comprises baking said base material to harden said coating.

6. The method of claim 4, wherein said baking is at about 100° to 250° for about 10 minutes.

7. The method of claim 1, wherein said backing includes an adhesive backing.

8. The method of claim 1, wherein said backing is removable by means of immersing said base material in a solvent.

9. The method of claim 8, wherein said backing is from the group of vinyl copolymers.

10. The method of claim 1, wherein the step of etching is by immersing said base material in a aqueous solution of hydrochloric acid and ferric chloride.

11. The method of claim 1, wherein the step of etching includes etching a channel within the base material suitable for the attachment of sutures.

12. The method of claim 1, further comprising heat treating the base material and removing the finished plurality of individual surgical needles from the base material.

13. The method of claim 12, wherein each surgical needle of the finished plurality of individual surgical needles is a curved, square bodied needle having a diameter of about 0.006 inches and an average bend movement of about 19 gram centimeters.

14. The method of claim 1, further comprising the step of removing said plurality of individual needle blanks from said etchant resistant backing.

15. A method for fabricating surgical needles comprising the steps of:
- selectively masking only a first side of an unmasked sheet of base material into chemically resistant patterns corresponding to a plurality of separate and independent surgical needles;
- exposing only unmasked areas of said first side masked base material to light of form an etchant resistant coating thereon;
- applying an adhesive etchant resistant backing to a second side of said base material to adhere said plurality of separate and independent surgical needles to said backing after etching and in preparation for chemical milling;
- etching away from said base material those areas which have not formed the etchant resistant coating and the adhesive etchant resistant backing to form a sheet with a plurality of separate and independent surgical needles attached thereto by said adhesive etchant resistant backing;
- removing said etchant resistant coating from said plurality of separate and independent surgical needles; and
- chemically milling away from said plurality of separate and independent surgical needles excess base material leaving said plurality of separate and independent surgical needles substantially free of rough edges, flairs and burrs.

16. The method of claim 15, wherein said masking comprises the steps of:
- coating said first side of said base material with a photoresistant material; and
- covering said first side of said coated base material with a negative image of a first side of said plurality of separate and independent surgical needles.

17. The method of claim 16, wherein said negative image is on a glass plate.

18. The method of claim 15, wherein the step of etching includes etching a channel within the base material suitable for the attachment of sutures.

19. The method of claim 15, wherein the step of chemically milling includes chemically sharpening and smoothing surfaces of said plurality of separate and independent surgical needles.

20. The method of claim 15, wherein said chemically milling is done in an amount sufficient to yield finished surgical needles with substantially no visible striations.

21. The method of claim 15, further comprising the step of removing said plurality of separate and independent surgical needles from said adhesive etchant resistant backing.

22. A method for fabricating surgical needles comprising the steps of:
- selectively masking only a first side of an unmasked sheet of base material into chemically resistant patterns corresponding to a plurality of unconnected surgical needles;
- exposing unmasked areas of said masked base material to light to form an etchant resistant coating thereon;
- etching away from said base material those areas which do not have said etching resisting coating thereon to form a sheet with a plurality of surgical needles spaced apart and not connected to any other base material attached to an etchant resistant backing;
- removing said etchant resistant coating from said etched base material; and
- chemically milling away from said base material leaving said plurality of unconnected surgical needles substantially free of rough edges, flairs and burrs.

* * * * *